United States Patent
Balachandran

(10) Patent No.: US 11,039,953 B2
(45) Date of Patent: Jun. 22, 2021

(54) DELIVERY SYSTEM

(71) Applicant: Chandrashekar Balachandran, Killara (AU)

(72) Inventor: Chandrashekar Balachandran, Killara (AU)

(*) Notice: Subject to any disclaimer, the term of this patent is extended or adjusted under 35 U.S.C. 154(b) by 142 days.

(21) Appl. No.: 16/199,144

(22) Filed: Nov. 24, 2018

(65) Prior Publication Data

US 2019/0159931 A1 May 30, 2019

(30) Foreign Application Priority Data

Nov. 24, 2017 (AU) ................................ 2017904745

(51) Int. Cl.
*A61F 9/00* (2006.01)
*A61F 2/16* (2006.01)
*A61F 2/14* (2006.01)
*A61K 9/00* (2006.01)

(52) U.S. Cl.
CPC ............ *A61F 9/0017* (2013.01); *A61F 2/148* (2013.01); *A61F 2/1667* (2013.01); *A61F 2/142* (2013.01); *A61K 9/0051* (2013.01)

(58) Field of Classification Search
CPC ...... A61F 9/0017; A61F 2/1667; A61F 2/148; A61F 2/142; A61K 9/0051
See application file for complete search history.

(56) References Cited

U.S. PATENT DOCUMENTS

| | | | |
|---|---|---|---|
| 5,494,484 A * | 2/1996 | Feingold | A61F 2/167 206/5.1 |
| 7,037,312 B2 * | 5/2006 | Kikuchi | A61F 2/167 606/107 |
| 9,539,139 B2 * | 1/2017 | Andino | A61M 5/346 |
| 9,687,340 B2 * | 6/2017 | Anderson | A61F 2/1675 |
| 10,182,906 B2 * | 1/2019 | Auld | A61F 2/167 |
| 2010/0057093 A1 * | 3/2010 | Ide | A61F 2/1662 606/107 |
| 2013/0085567 A1 * | 4/2013 | Tan | A61F 2/148 623/5.12 |
| 2013/0245554 A1 | 9/2013 | Inoue et al. | |

FOREIGN PATENT DOCUMENTS

| | | |
|---|---|---|
| CH | 708083 A1 | 11/2014 |
| EP | 2111821 A1 | 10/2009 |
| GB | 2521360 A | 6/2015 |
| WO | 2008141309 A1 | 11/2008 |

OTHER PUBLICATIONS

European Search Report—European Application No. 18208064.8 dated Apr. 23, 2019, 8 pages.

* cited by examiner

*Primary Examiner* — Julian W Woo
(74) *Attorney, Agent, or Firm* — Sunstein LLP

(57) ABSTRACT

A delivery system for an ocular implant includes a delivery tube having a delivery end with an opening and a control end. A delivery device fits at least partially within the delivery tube. The delivery device is configured to contact the ocular implant and control the position of the ocular implant within the delivery tube. The delivery system includes a fluid inlet nozzle that injects fluid into the delivery tube between the control end and the ocular implant. The injected fluid flows around the sides of the ocular implant and out from the delivery end of the delivery tube.

17 Claims, 5 Drawing Sheets

DELIVERY SYSTEM

This application claims priority to Australian Patent Application 2017904745, filed Nov. 24, 2017, which is incorporated herein by reference in its entirety.

FIELD OF THE INVENTION

The present invention relates to a syringe and, in particular, to a syringe for delivering an ocular implant into an eye during eye surgery.

BACKGROUND

In eye surgery, controlled delivery of ocular implants into the eye can be critical to the success of the surgery. In particular, in Descemet Membrane Endothelial Keratoplasty (DMEK) in which a corneal endothelial implant is delivered into the anterior chamber for grafting onto the rear side of the cornea, careful delivery of the implant is essential due to the delicate nature of the implant and accurate positioning. Currently, fluid syringes connected to pipettes are used to delivery DMEK grafts but these grafts tend to be squirted into the eye in a poorly controlled manner which has a negative effect on the chance of the success of the surgery.

Screw type delivery in syringes has been used in Inter Ocular Lens (IOL) implants in which an artificial lens is used to replace a damaged lens, for example due to cataract. However, in IOL delivery devices fluid is not required. Typically viscoelastic material is used. In DMEK surgery viscoelastic material is not suitable for use as will prevent the graft from sticking to the cornea once the DMEK graft has entered the eye.

SUMMARY OF THE INVENTION

In a first aspect the invention provides a delivery system for an ocular implant comprising:
  a delivery tube having a delivery end and a control end, the delivery end comprising an opening;
  a delivery device configured to fit at last partially within the delivery tube, the delivery device configured to contact the ocular implant and control the position of the ocular implant within the delivery tube; and
  a fluid inlet nozzle, the fluid inlet nozzle configured to inject fluid into the delivery tube between the control end and the ocular implant;
  wherein the delivery system is configured such that the injected fluid flows around the sides of the ocular implant and out from the delivery end of the delivery tube.

In such embodiments the flow of fluid around the sides of the ocular implant and the contact to the ocular implant enable the position of the ocular implant within the delivery tube to be controlled. This provides controlled delivery of the ocular implant from the delivery system into an eye.

In embodiments, the system is configured such that the flow of the injected fluid prevents contact between the ocular implant and internal walls of the delivery tube.

By preventing contact of the ocular implant and the walls of the delivery tube, damage to the ocular implant during delivery from the delivery system is reduced.

In embodiments, the delivery device comprises:
  a screw, a screw having a first thread;
  the tube having a second thread;
  wherein the system is configured such that the first thread of the screw engages the second thread of the tube and rotation of the screw projects the screw within the tube.

Screw type delivery converting rotational movement of the screw to its lateral position within the tube provides improved control over delivery of the ocular implant.

In embodiments, the delivery device further comprises a fixing device, the fixing device configured such that rotation of the screw does not create rotation of the fixing device, the fixing device being configured to contact the ocular implant. This arrangement provides the advantage that the system provides controlled lateral movement of the fixing device and ocular implant within the delivery tube using the screw delivery system without creating any rotational movement of the fixing device and ocular implant which could, potentially, cause damage to the delicate ocular implant.

In embodiments the screw comprises a cavity, the cavity housing the fixing device.

In embodiments, the fixing device is a needle.

In embodiments, the tube contains at least one strut, the strut extending from at least one internal wall of the tube, the strut configured to support the fixing device.

Such embodiments provide controlled positioning of the delivery device within the delivery tube. For example, the strut may be configured such that the delivery device is maintained in a central position within the delivery tube. Such control of the delivery device and, consequently, the ocular implant, enables accurate positioning of the ocular implant and improved alignment of the implant with the opening of the delivery tube for delivery.

In embodiments, the delivery end of the delivery tube is tapered towards the opening. This embodiment provides an opportunity for accurate positioning and delivery of the ocular implant into the eye. Additionally, for example in DMEK surgery using corneal grafts, movement of the ocular implant into the tapered section results in a slow rolling of the graft away from the wall to create a scroll type configuration of the graft for delivery through the opening into the eye.

In embodiments, the delivery tube has a closable access window between the fluid inlet nozzle and the opening, the closable access window suitable for receiving the ocular implant.

The closable access window enables the ocular implant to be inserted into the delivery tube and connected to the delivery device. The access window can then be closed and fluid injected into the delivery system to allow delivery of the ocular implant into the eye.

In embodiments, the ocular implant is a DMEK graft.

In a second aspect, a method is disclosed of delivering an ocular implant to an eye, the method comprising:
  providing a delivery system positioning at least a portion of a delivery device within a delivery tube, the delivery tube having a delivery end and a control end, the delivery end comprising an opening;
  positioning the delivery device relative to the delivery tube to contact an ocular implant;
  controlling the position of the ocular implant within the delivery tub with the delivery device;
  injecting fluid into a fluid inlet nozzle between the ocular implant and the control end in fluid communication with the delivery tube;
  allowing the injected fluid to flow around the sides the ocular implant to the delivery end.

In some embodiments, the system is configured such that the flow of the injected fluid prevents contact between the ocular implant and internal walls of the delivery tube.

In some embodiments, the method further comprises rotating the delivery device relative to the delivery tube to move the ocular implant towards the delivery end.

In some embodiments, the method further comprises contacting at least a portion of the ocular implant with the fixing device.

In some embodiments, the method further comprises, during rotation of the delivery device, laterally moving the fixing device and the ocular implant towards the delivery end.

DETAILED DESCRIPTION OF THE DRAWINGS

We now describe various example embodiments of the invention. Embodiments of the invention are configured to deliver ocular implants into an eye. Different types of eye surgeries require the delivery of different types of implants into the eye. In intraocular lens surgery an intraocular lens (IOL) is inserted into the eye to replace the eye's natural lens. This procedure is often performed as cataract surgery. A second type of eye surgery is Descemet Membrane Endothelial Keratoplasty (DMEK). DMEK surgery involves the transplantation of corneal endothelial cells on the rear surface of the cornea. The DMEK graft is delivered into the anterior region of the eye behind the cornea and grafted to the rear surface of the cornea.

The requirements and surgical conditions for different surgeries vary. In IOL surgery the replacement lens is synthetic and relatively robust. Controlled delivery of the replacement lens into the eye is important to correctly position the lens and to avoid damage to the lens and lens capsule. However, the relative robustness and synthetic nature of the lens means that physical contact can be made to the lens without reducing the chances of successful operation, unless the contact results in scratching of the lens. In contrast, DMEK surgery is a considerably more delicate procedure. The DMEK graft is typically 5-20 microns thick and consists of a disk having a diameter of around 9 mm. The surface of the disk is covered with living endothelial cells. Any contact to the cells can destroy. Thus, careful handling of the graft is essential in DMEK surgery. Additionally, correct positioning of the graft within the anterior region of the eye is also important in order to increase the chances of success of the surgery.

Figure 1:
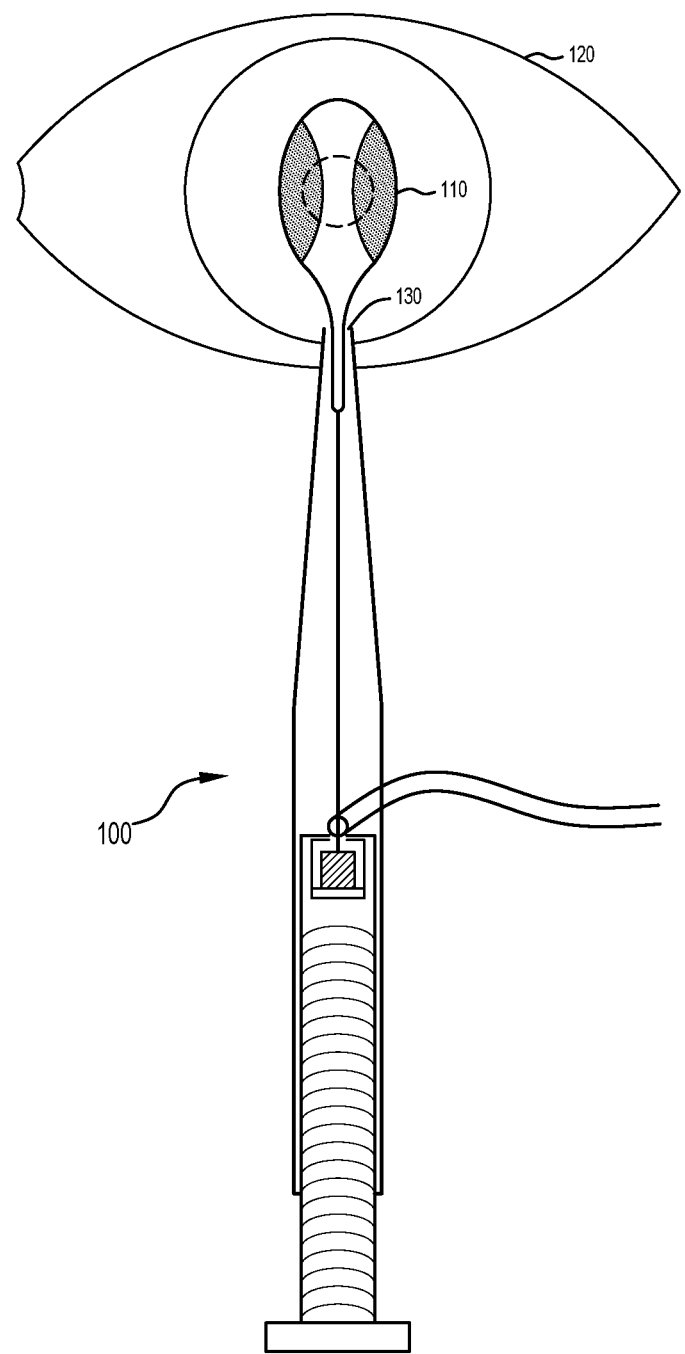
FIG. 1 shows delivery of an ocular implant into the eye using an embodiment of the invention.

FIG. 1 illustrates an embodiment of the invention in use in delivering a graft into an eye during DMEK surgery. Delivery system 100 (described in detail below) is shown delivering graft 110 into eye 120. FIG. 1 shows a front view of the eye. Opening 130 of delivery system 100 is inserted through a slit in the cornea. The slit provides access to the anterior chamber of the eye. Graft 110 is delivered into the anterior chamber by delivery device 100. Delivery device 100 provides controlled delivery of graft 110 into the eye.

Figure 2:
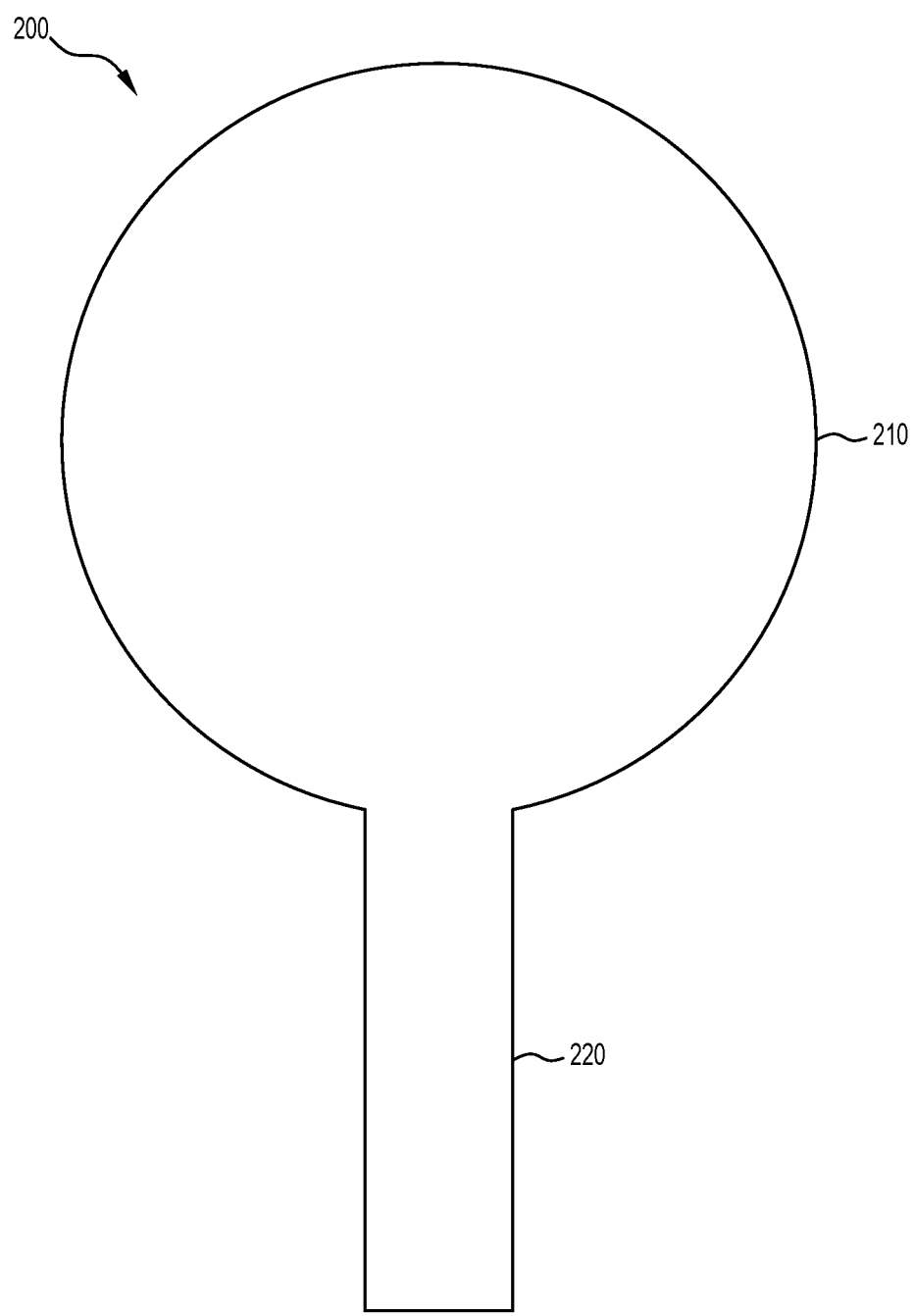
FIG. 2 is an illustration of a DMEK implant.

FIG. 2 shows an example of a DMEK implant 200. The implant is generally keyhole shaped including a disk shaped portion 210 and a tail shaped extension 220. The tail portion extends from the edge of the disk shaped portion. The DMEK implant is cut from a donor cornea, typically using a trephine. In preferred embodiments the disk shaped portion 210 largely contains corneal endothelial tissue cut from the rear surface of a donor cornea. Tail section 220 extends from the endothelial region of the cornea into the sclera portion of the eye. At least part of tail section is sclera. The junction between the endothelial tissue and sclera is preferably positioned within the tail section 220 of the implant.

Dimensions of the implant vary depending on the size of the eye undertaking surgery but typical dimensions are around 9 mm diameter for the disc portion of the implant. The tail portion has a width of around 2 mm and length of around 2 mm. The embodiment of FIG. 2 is for illustrative purposes only. In practice, the shape of the implant may vary. For example the disk portion may not be round but, oval or other shape and the various proportions of the implant may also vary.

The keyhole shape of the implant is particularly beneficial for DMEK surgery. The tail section is typically not required for grafting and so provides a region of the implant that can be manipulated, including being held or attached, without concerns about damaging endothelial cells on this part of the implant. The tail region can be manipulated in order to position the disk of the implant carefully into position within the eye.

Figure 3:
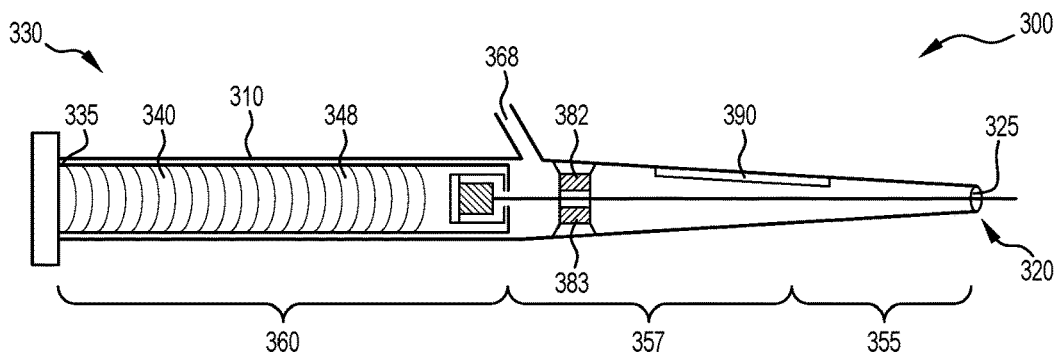
FIGS. 3 and 4 illustrate a first embodiment of the invention.
Figure 4:
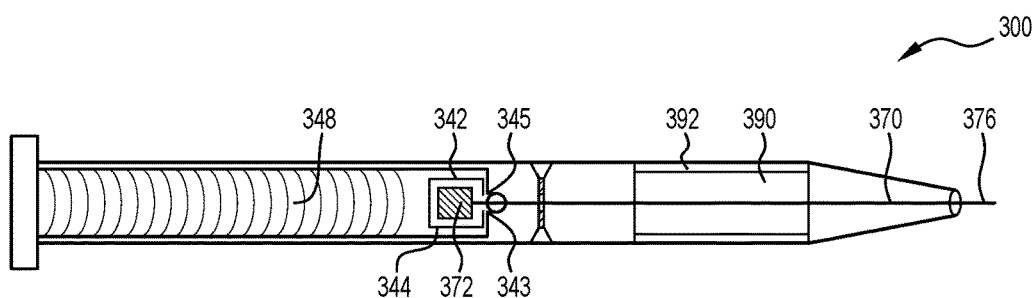

FIGS. 3 and 4 illustrate a first embodiment of a delivery system for delivering an ocular implant into an eye. The embodiment of FIGS. 3 and 4 is particularly useful for delivery of DMEK implants but may also be used for other types of eye surgery including IOL surgery.

FIG. 3 shows a side view of delivery system 300. FIG. 4 shows a top view of delivery system 300. The equivalent parts of the delivery system 300 are labelled using equivalent numbering in both figures.

The delivery system comprises a delivery tube 310. Tube 310 has a delivery end 320. Opening 325 is positioned at delivery end 320 and configured for delivery of an ocular implant from within the delivery tube through opening 325 into an eye for surgery. Tube 310 has a control end 330. Control end 330 has an opening 335. Opening 335 is configured to receive delivery device 340 for controlling the position of the ocular implant within the delivery tube and out of the delivery tube into the eye for surgery.

In the examples of in embodiment of FIGS. 3 and 4 the delivery system is configured as a syringe with the delivery tube 310 being a barrel and delivery device 340 being a screw type plunger. Delivery tube 310 is generally circular in cross section. Delivery tube has a rear section 360 having a generally cylindrical configuration. Rear section 360 is primarily configured to house delivery device 340.

Delivery tube 310 has delivery section 355 at the delivery end of the tube. The delivery tube is tapered within the delivery region 350. The taper is inclined towards opening 325 to reduce the cross sectional diameter of the delivery tube towards opening 325.

Delivery section 355 forms part of forward section 350. In the embodiment of FIGS. 3 and 4, delivery tube 310 is tapered in the vertical direction through the entire forward section 350, as illustrated in FIG. 3. However in the horizontal direction the forward region is tapered only within delivery section 355, as shown in FIG. 4.

In further embodiments of the invention the delivery tube will include a constant taper throughout the forward region creating a cone shaped tube towards opening 325.

Delivery tube 310 includes a fluid inlet nozzle 368. Fluid inlet nozzle 370 is positioned within forward section 350 of delivery tube 310. Fluid inlet nozzle 368 is configured to be connectible to an irrigating tube. Fluid inlet nozzle 368 allows fluid to be injected into delivery tube 310.

Forward section 350 includes a loading chamber 357. Loading chamber 357 includes a lid 390. Lid 390 is a closable access window providing access into delivery tube 310. In the embodiment of FIGS. 3 and 4 lid 390 is hinged along an edge 392. In further embodiments the lid may be hinged along a different edge. Alternatively the lid may be completely removable from the delivery tube.

Delivery device 340 is a screw type plunger 348. Plunger 348 includes a thread on its outer surface. This thread is arranged to engage with a thread positioned on the internal surface of delivery tube 310 in rear section 360 of the delivery tube. Rotation of plunger 348 within the delivery tube results in lateral movement of plunger 348 along the central axis of delivery tube 310. The position of plunger 348 within the delivery tube 310 is controlled by rotation of plunger 348.

Delivery device 340 includes needle 370. Needle 370 is an example of a fixing device that forms part of the delivery device 340.

Needle 370 is attached to plunger 348 using a cavity housing. As shown in the embodiments of FIGS. 3 and 4, needle 370 has an extended shoulder portion 372. In FIGS. 3 and 4 the shoulder portion is cylindrical and has an extended diameter compared with needle 370. Plunger 348 has a receiving cavity 342 configured to receive shoulder portion 372. Cavity 342 includes an opening 343 to enable needle 370 to extend forward into forward portion of delivery tube 310. Abutment surface 345 extends from the outer sides of the plunger 348 to opening 343. The depth of the cavity within plunger 348 is defined between abutment surface 345 and rear surface 348. Cavity 342 includes access opening 344 to enable shoulder portion 372 to be positioned into cavity.

In the embodiment of FIGS. 3 and 4 the cavity is positioned to enable the central axis of needle 370 to be collocated with central axis of plunger 348 and delivery tube 310.

The cavity is arranged to receive shoulder portion 372 of needle 370 tightly to prevent lateral movement of needle 370 with respect to plunger 348. Lateral movement of plunger 348 within delivery tube 310 produces equivalent lateral movement of needle 370. In the examples of FIGS. 3 and 4 shoulder portion 372 is cylindrical. In further embodiments of the invention the cavity and connection point may be any interacting shape.

The cylindrical shoulder portion and interacting cavity section are configured such that plunger 348 can rotate within delivery tube 310 without producing a rotating force on needle 370. Thus, rotation of plunger 348 produces lateral movement of needle 370 without rotational movement of needle 370. The system is designed such that there is no significant rotational friction between connection point 372 and cavity 340.

In further embodiments frictional force between these components may be allowed in order to produce a rotational force on the needle. In further embodiments the screw plunger and needle may be integral.

Struts 382, 383 are positioned within the delivery tube 310. Struts 382, 383 are arranged to maintain the position of needle 370 along the central axis of the delivery tube. The needle is held between the struts to maintain a straight length. The struts may have multiple configurations.

The dimensions of the embodiment of FIGS. 3 and 4 are as follows:

The delivery tube 310 has a 12 mm diameter within the cylindrical rear section 330.
The length of the cylindrical rear section is 70 mm.
Opening 325 at the delivery end is 2 mm in diameter.
Loading chamber 357 has a length of 30 mm.
Delivery portion 355 has a length of 25 mm.

In use the plunger 348 and needle 370 are assembled and inserted into control end 330 of delivery tube 310. The delivery device is moved laterally within the delivery tube such that tip 376 of needle 370 is positioned in the proximity of lid 390. Lid 390 is opened and DMEK graft is inserted into the loading chamber 357. Once the graft is placed inside, its tail region 220 is pegged by the needle tip 376. By pegging the needle tip to the DMEK graft, the position of the DMEK graft can be controlled by the delivery device. The graft may be stained with methylene blue.

After insertion of the graft, the lid can be closed to seal the loading chamber of the delivery system. Fluid is then delivered through fluid inlet nozzle. The fluid is delivered behind struts 382 383 to allow equal distribution of fluid above and below the graft and to prevent the graft from coming away from the needle.

The injected fluid flows around the sides of the graft and out from the delivery end 325. The flow of the injected fluid prevents contact between the ocular implant and the walls of the delivery tube. In preferred embodiments the fluid is trickled in at a slow rate to form a laminar flow through the forward region of the delivery device. Typical flow rate may be 1 mm per minute. It is expected the slow laminar flow rate will, while keeping the graft pegged on the needle, float the graft way from the floor, roof and side walls of the injector device. This would ensure that the endothelial cells are not mechanically damaged by making mechanical contact with the wall. The floated graft will be progressed toward the tip by twisting the plunger. The laminar flow also has the benefit of washing the graft of any microbial or chemical contaminants.

Screw plunger 348 is twisted to move the graft to the delivery section of the tube. The delivery section includes a slow taper. As the graft approaches the tapered end of the delivery device the volume of laminar fluid passing through a smaller cross-sectional area of the delivery device would encourage the graft to form a scroll before arriving at the opening 325.

Continued rotation of the screw plunger 348 results in the graft being pushed through opening 325 and through the corneal incision into the eye. The delivery device walls are thinned at the end so as to allow the scroll to pass and the needle to extrude out of the delivery device even if this requires a physical expansion by the needle. This would prevent the needle from getting stuck inside.

After extraction from the delivery device and into the eye the tail of the graft may be removed from the tip of the needle and further surgery may be performed in order to position the graft correctly into the eye to allow the implant to take place.

The fluid in the injector device may be balanced salt solution which has the nutrients appropriate for the graft and recipient eye. The fluid can be exchanged with methylene blue again if needed to re-stain the graft prior to implantation. The incision in the cornea is larger than the size of the delivery tip to allow fluid to leak out of the eye around the delivery device or alternatively a separate incision can be made to allow fluid leak from the eye. A benefit of this leak is to allow delivery of the graft without raising the intraocular pressure and thereby preventing graft extrusion after placing the graft in the eye.

The delivery device has the advantage that just before delivering the graft an equilibrium can be achieved whereby, the laminar flow keeps the graft afloat, the anterior chamber of the eye is irrigated and kept formed and the surgeon has the opportunity to keep the intraocular pressure at an acceptable low steady state. The anterior chamber by being irrigated and kept "formed" is not collapsed and the iris is not in contact with the cornea which would prevent the insertion of the graft. This is important for a controlled delivery of the graft. The inflow fluid rate can be altered to deepen the anterior chamber by the appropriate amount and the surgeon can deliver the graft when once he/she is ready and confident of success.

The injector will be made of transparent material to allow visualisation of the graft throughout its journey. If at any time the surgeon is unhappy with the loading and delivery then the design allows the surgeon to eject the graft without implantation or to rewind the plunger and reload the graft without causing trauma to the graft. It may be made of materials such as plastic coated with materials or glass with properties that keep the graft away from the injector's internal surface. These will also achieve transparency.

Figure 5:
FIGS. 5 and 6 illustrate a second embodiment of the invention.
Figure 6:
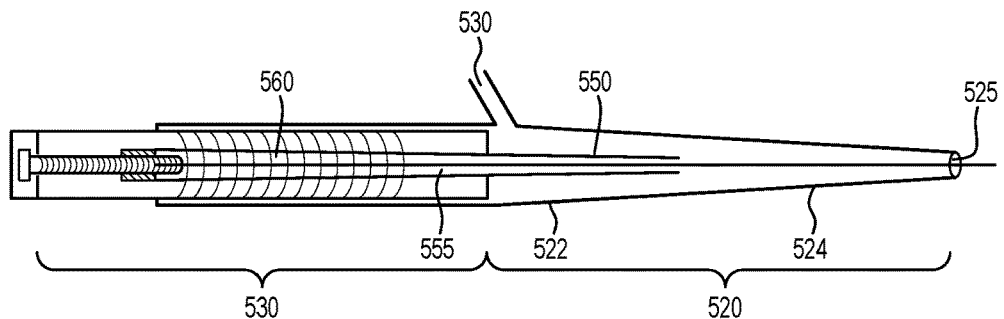

FIGS. 5 and 6 show a second embodiment of the invention. In the embodiment of FIGS. 5 and 6 the many of the parts of the delivery system are the same as those previously described with respect to the embodiment of FIGS. 3 and 4. In particular, the delivery tube 500 includes rear portion 530 comprising a cylindrical tube portion. The forward region 520 extends towards opening 525. Forward region 520 includes a loading region 522 and a delivery region 524 extending to opening 525. Loading region 522 includes fluid inlet nozzle 530 and lid 540.

The main difference between the embodiments of FIGS. 3 and 4 and that of FIGS. 5 and 6 is the delivery mechanism. In the embodiment of FIGS. 5 and 6 a forcep 550 is used to peg the tail of the graft. The forcep 550 is used with sleeve 560. The sleeve is used to close the forcep. Sleeve 560 is moved down forcep 550 using a screw. Forcep 550 includes a pivot 555. The sleeve is moved down the forcep using a screw. The distance from the pivot results in greater or less closure or forceps 550 in order to peg and unpeg the tail of the graft. A second screw is used to move the sleeve and forcep configuration down the barrel of the delivery tube.

The embodiment of FIGS. 5 and 6 may not require a strut depending on the rigidity of the sleeve and forcep configuration. If the forcep and sleeve has sufficient rigidity the forcep may be strong enough to hold a straight line through the barrel of the delivery tube. However, in further embodiments struts may be used to position the forceps along the central axis along the delivery tube.

The embodiment of FIGS. 5 and 6 is operated in a similar manner to that of the embodiment of FIGS. 3 and 4. Specifically, the sleeve and forceps are moved along the barrel of the delivery tube in order that the tip of the forceps is positioned in the vicinity of the loading chamber. A graft is entered into the loading chamber and the tail of the graft is pegged using the tip of the forceps. Once the graft is securely pegged the lid is closed and fluid is injected through fluid inlet nozzle 530 in order to provide equal distribution of fluid above and below the graft. Preferably, the fluid is injected in a manner to produce laminar flow through the barrel of the delivery tube and through opening 525. The position of the graft within the barrel is controlled using the second screw. As the graft is moved towards the opening the taper of the delivery tube forces the graft into a scroll configuration and controls the delivery of the graft through the opening and into the eye.

Figure 7:
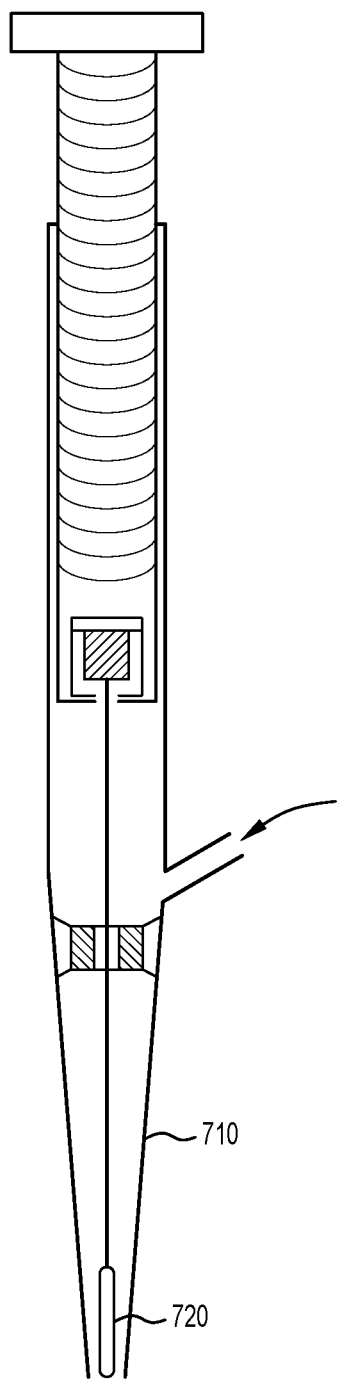
FIGS. 7 and 8 illustrate a graft positioned within an embodiment of the invention.
Figure 8:
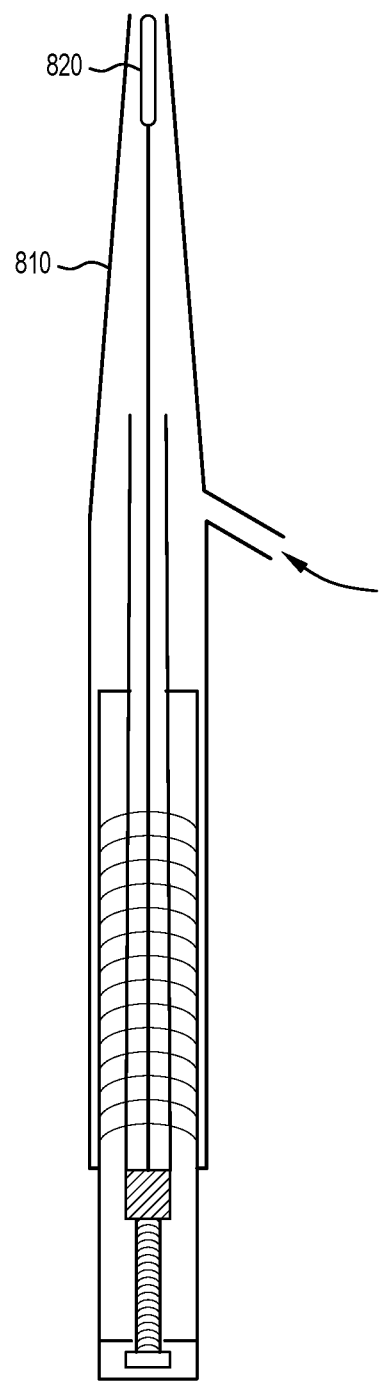

FIGS. 7 and 8 illustrate the graft 720 820 loaded in the delivery tube 710 810 and positioned by the opening. Further movement of the graft will eject the graft from the delivery tube.

It will be clear to those skilled in the art that the embodiments described above provide specific examples of the invention. Further embodiments exist having different dimensions and variations to the embodiments described above.

Embodiments of the invention provide a delivery system for an ocular implant which enables control of the delivery of the ocular implant from the delivery tube into the eye. The injection of fluid behind the graft and the equal flow of fluid around the graft enables the graft to be moved within the delivery tube and through the opening without the graft contacting the internal walls of the delivery tube. This reduces the chances of damaging the delicate endothelium cells which may become damaged upon contact with the internals walls of the tube. The screw type plunger which is configured to provide lateral movement of the graft through the tube without rotational movement provides controlled lateral positioning of the graft without excessive rotation of the graft which may lead to damage to the endothelial cell.

The embodiments above have been described in particular with reference to DMEK surgery. However, it will be clear to those skilled in the art that embodiments of the invention may be used for different types of surgery in particular those which require careful positioning and control of implants for delivery. Further embodiments of the invention may be used for other purposes beyond eye surgery.

Embodiments also include a method of delivering an ocular implant to an eye using the delivery system described herein.

The method includes the following steps:
providing a delivery system positioning at least a portion of a delivery device within a delivery tube, the delivery tube having a delivery end and a control end, the delivery end comprising an opening;
positioning the delivery device relative to the delivery tube to contact an ocular implant;
controlling the position of the ocular implant within the delivery tub with the delivery device;
injecting fluid into a fluid inlet nozzle between the ocular implant and the control end in fluid communication with the delivery tube; and
allowing the injected fluid to flow around the sides the ocular implant to the delivery end.

It is to be understood that, if any prior art publication is referred to herein, such reference does not constitute an admission that the publication forms a part of the common general knowledge in the art, in Australia or any other country.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:

1. A delivery system for an ocular implant comprising:
a delivery tube having an axis, a delivery end, and a control end, the delivery end comprising an opening;

a delivery device configured to fit at least partially within the delivery tube, the delivery device being moveable along the axis of the delivery tube and having a fixing device, the fixing device having an attachment point configured to be pegged to an ocular implant and control the position of the ocular implant within the delivery tube; and the delivery system comprising a fluid inlet nozzle, the fluid inlet nozzle positioned between the control end and the attachment point, the fluid inlet nozzle configured to inject fluid into the delivery tube and create a fluid path from the inlet nozzle, through the delivery tube, and out from the opening of the delivery end;

wherein the delivery system is configured such that in use, an ocular implant is pegged to the fixing device, fluid is injected through the inlet nozzle to create a flow of fluid along the fluid path and around the ocular implant, and by pegging the fixing device to the ocular implant, the delivery device is configured to change the position of the ocular implant within the flow of fluid.

2. A delivery system according to claim 1 wherein the system is configured such that when fluid is injected into the fluid inlet nozzle, the flow of the injected fluid prevents contact between the ocular implant and internal walls of the delivery tube.

3. A delivery system according to claim 1 wherein:
an internal surface at the control end of the delivery tube comprises a thread;
the delivery device comprising a screw type plunger having a thread on its outer surface;
wherein the thread of the plunger is arranged to engage with the thread of the delivery tube and so that rotation of the plunger with respect to the delivery tube results in relative movement of the plunger along an axis of the delivery tube.

4. The delivery system of claim 3, wherein the fixing device is configured such that rotation of the plunger within the delivery tube does not create rotation of the fixing device.

5. A delivery system according to claim 4, wherein the plunger comprises a cavity, the cavity housing the fixing device.

6. A delivery system according to claim 5 wherein the fixing device is a needle.

7. The delivery system according to claim 1, wherein the delivery tube contains at least one strut, the strut extending from at least one internal wall of the delivery tube, the strut configured to support the fixing device.

8. A delivery system according to claim 1 wherein the ocular implant is a DMEK graft.

9. A method of delivering an ocular implant to an eye, the method comprising:
providing a delivery system for an ocular implant according to claim 1;
attaching an ocular implant to the fixing device within the delivery tube and positioning the ocular implant between the fluid inlet nozzle and the opening of the delivery end;
injecting fluid into the fluid inlet nozzle to create a flow of fluid through the delivery tube and out from the opening of the delivery end; and
controlling the position of the ocular implant within the flow of fluid using the delivery device.

10. A method according to claim 9, wherein the system is configured such that the flow of the injected fluid prevents contact between the ocular implant and internal walls of the delivery tube.

11. A method according to claim 9, further comprising rotating the delivery device relative to the delivery tube to move the ocular implant towards the delivery end.

12. The method of claim 9 wherein the ocular implant is a DMEK graft.

13. The method of claim 9 wherein injection of fluid creates a flow of fluid through the delivery tube, around the ocular implant, and out from the opening of the delivery end, allowing the ocular implant to float within the fluid within the delivery tube.

14. The method of claim 9 comprising the further step of controlling the injection of fluid to create a laminar flow of fluid through the delivery device.

15. The system of claim 1 wherein the injected fluid creates a flow of fluid through the delivery tube, around the ocular implant, and out from the opening of the delivery end, allowing the ocular implant to float within the fluid within the delivery tube.

16. The delivery system of claim 1 wherein the attachment point is the tip.

17. The delivery system of claim 1 wherein the fixing device is a forcep.

* * * * *